US007867755B2

(12) United States Patent (10) Patent No.: US 7,867,755 B2
Joos et al. (45) Date of Patent: Jan. 11, 2011

(54) METHOD FOR ANALYZING PROTEINS

(75) Inventors: Thomas Joos, Tübingen (DE); Dieter Stoll, Reutlingen (DE)

(73) Assignee: NMI Naturwissenschaftliches und Medizinisches Institut an der Universität Tübingen, Reutlingen (DE)

( * ) Notice: Subject to any disclaimer, the term of this patent is extended or adjusted under 35 U.S.C. 154(b) by 691 days.

(21) Appl. No.: 10/426,093

(22) Filed: Apr. 29, 2003

(65) Prior Publication Data

US 2004/0029292 A1 Feb. 12, 2004

Related U.S. Application Data

(63) Continuation of application No. PCT/EP01/12295, filed on Oct. 24, 2001.

(30) Foreign Application Priority Data

Oct. 31, 2000 (DE) ................. 100 54 055

(51) Int. Cl.
*C12M 3/00* (2006.01)
(52) U.S. Cl. .................................. 435/287.2
(58) Field of Classification Search ................. 435/174, 435/262, 961–969, 971–973; 436/512, 536, 436/543, 547, 815, 825; 424/130.1, 141.1, 424/184.1, 185.1
See application file for complete search history.

(56) References Cited

U.S. PATENT DOCUMENTS

| 4,478,744 | A | * | 10/1984 | Mezei et al. ................ 530/322 |
| 4,658,022 | A | * | 4/1987 | Knowles et al. ............. 530/402 |
| 4,970,171 | A | * | 11/1990 | Messenger et al. ............ 436/66 |
| 5,061,790 | A | * | 10/1991 | Elting et al. ................ 530/402 |
| 5,223,441 | A | * | 6/1993 | Ullman et al. .............. 436/547 |
| 5,449,601 | A | * | 9/1995 | Jean et al. ...................... 435/5 |
| 5,565,332 | A | | 10/1996 | Hoogenboom et al. |
| 5,708,155 | A | | 1/1998 | Potter et al. |
| 5,723,129 | A | | 3/1998 | Potter et al. |
| 5,763,158 | A | | 6/1998 | Bohannon |
| 5,790,155 | A | | 8/1998 | Usui et al. |
| 5,798,155 | A | | 8/1998 | Yanagawa et al. |
| 5,849,531 | A | | 12/1998 | Potter |
| 5,872,234 | A | | 2/1999 | Bandman et al. |
| 5,955,317 | A | | 9/1999 | Suzuki et al. |
| 5,961,923 | A | | 10/1999 | Nova et al. |
| 6,113,897 | A | * | 9/2000 | Dano et al. ................ 424/130.1 |
| 6,197,599 | B1 | * | 3/2001 | Chin et al. ................... 436/518 |
| 6,225,047 | B1 | * | 5/2001 | Hutchens et al. ................ 435/5 |
| 6,261,569 | B1 | | 7/2001 | Comis et al. |
| 6,329,209 | B1 | | 12/2001 | Wagner et al. |
| 6,365,418 | B1 | | 4/2002 | Wagner et al. |
| 6,406,921 | B1 | | 6/2002 | Wagner et al. |
| 6,420,125 | B1 | | 7/2002 | Fledelius et al. |
| 6,794,363 | B2 | * | 9/2004 | Bejanin et al. ................ 514/12 |
| 6,897,073 | B2 | | 5/2005 | Wagner et al. |
| 6,955,915 | B2 | * | 10/2005 | Fodor et al. ................ 435/289.1 |
| 7,022,486 | B2 | | 4/2006 | Campbell |
| 7,645,586 | B2 | * | 1/2010 | Gordon et al. ................ 435/7.1 |
| 2002/0042386 | A1 | | 4/2002 | Rosen et al. |
| 2002/0055186 | A1 | * | 5/2002 | Barry et al. .................. 436/518 |
| 2002/0081617 | A1 | | 6/2002 | Buranda et al. |
| 2002/0106702 | A1 | | 8/2002 | Wagner et al. |
| 2002/0110843 | A1 | | 8/2002 | Dumas |
| 2002/0110933 | A1 | | 8/2002 | Wagner et al. |
| 2002/0119579 | A1 | | 8/2002 | Wagner |
| 2002/0137119 | A1 | * | 9/2002 | Katz ............................ 435/23 |
| 2003/0028330 | A1 | | 2/2003 | Cheng et al. |
| 2003/0032039 | A1 | | 2/2003 | Cunningham et al. |
| 2003/0044862 | A1 | | 3/2003 | Giaccia et al. |
| 2003/0054408 | A1 | * | 3/2003 | Ravi et al. .................... 435/7.1 |
| 2003/0143612 | A1 | | 7/2003 | Ault-Riche et al. |
| 2004/0029292 | A1 | * | 2/2004 | Joos et al. .................... 436/518 |
| 2004/0229284 | A1 | | 11/2004 | Luciw et al. |
| 2005/0153298 | A1 | | 7/2005 | Gembitsky et al. |
| 2005/0214304 | A1 | | 9/2005 | Pastan et al. |

FOREIGN PATENT DOCUMENTS

| DE | 40 23 945 | 1/1992 |
| EP | 0 267 355 | 3/1987 |
| EP | 0 337 057 | 1/1989 |
| JP | 07285999 | 10/1995 |
| WO | WO 96/05847 | 2/1996 |
| WO | WO-96/05847 A1 | 2/1996 |
| WO | WO-96/29629 A2 | 9/1996 |

(Continued)

OTHER PUBLICATIONS

Shea EA & Cohen MP, Immunologic detection and measurement of glycated apolipoprotein B with site specific monoclonal antibodies. J. Immunol. Methods. Jun. 1993;162(1):85-95.*

(Continued)

*Primary Examiner*—Ann Y Lam
(74) *Attorney, Agent, or Firm*—Goodwin Procter LLP

(57) ABSTRACT

A method for analyzing proteins makes use of an array of first capture molecules which are specific for peptide epitopes. The proteins to be analyzed or a protein mixture containing the proteins to be analyzed is degraded to peptide fragments corresponding to the peptide epitopes, after which the array of capture molecules is incubated with the peptide fragments. The peptide fragments bound to the capture molecules are then detected.

18 Claims, No Drawings

FOREIGN PATENT DOCUMENTS

| WO | WO-97/07132 A1 | 2/1997 |
|---|---|---|
| WO | WO-99/38013 | 7/1999 |
| WO | WO-9939210 | 8/1999 |
| WO | WO-00/04389 A2 | 1/2000 |
| WO | WO-00/04389 A3 | 4/2000 |
| WO | WO 00/45168 | 8/2000 |
| WO | WO-00/45168 A1 | 8/2000 |
| WO | WO-00/54046 A2 | 9/2000 |
| WO | WO-01/78652 | 10/2001 |
| WO | WO-0206834 | 1/2002 |
| WO | WO-02/25287 A2 | 3/2002 |
| WO | WO-03/058249 A1 | 7/2003 |

OTHER PUBLICATIONS

Maggio ET. Enzyme-immunoassay, pp. 53-70, CRC Press, Inc., (1980).*

Harper et al., Two-Dimensional Gel Electrophoresis, Unit 10.4, Current Protocols in Protein Science (1998), pp. 10.4.1 to 10.4.36.*

Maggio, E.T. Enzyme-Immunoassay, Chapters 3 and 9, CRC Press, Inc. (1980). (pp. 53-70 and 181-196).*

Chou et al., "Prediction of Protein Conformation," *Biochemistry*, vol. 13, No. 2, pp. 222-245, (1974).

Devereux et al., "A comprehensive set of sequence analysis programs for the VAX", *Nucleic Acids Research*, vol. 12, No. 1, pp. 387-395, (1984).

Geng et al., "Signature-peptide approach to detecting proteins in complex mixtures," *Journal of Chromatography*, vol. 870, pp. 295-313, (2000).

Grimm et al., "Nanogram scale separations of proteins using capillary high-performance liquid chromatography with fully-automated on-line microfraction collection followed by matrix-assisted laser desorption ionisation time-of-flight mass spectrometry, protein sequencing and Western blot analysis." *Journal of Chromatography* vol. 800, pp. 83-88, (1998).

Hennig, WinPep-ein Programm zur Analyse von Aminosäuresequenzen, *Biospektrum*, vol. 4, No. 5, pp. 49-50 (1998).

Hopp et al., "A Computer Program for Predicting Protein Antigenic Determinants," *Molecular Immunology*, vol. 20, No. 4, pp. 483-489, (1983).

Jean et al., "A novel protein immunoassay with predetermined specificity using monoclonal antibodies against tryptic fragments: application to HIV P24 antigen," *Journal of Immunological Methods*, vol. 185, pp. 103-114, (1995).

Kyte et al., "A Simple Method for Displaying the Hydropathic Character of a Protein," *J. Mol. Biol.*, vol. 157, pp. 105-132, (1982).

Levilliers Nicolette et al., "Monoclonal and polyclonal antibodies detect a new type of post-translational modification of axonemal tubulin." *Journal of Cell Science*, vol. 108, No. 9, pp. 3013-3028, (1995).

Phelps et al., Metabolomics and Microarrays for Improved Understanding of Phenotypic Characteristics Controlled by Both Genomics and Environmental Constraints. Curr. Opi. Biotech. 13(1): 20-24, 2002.

Arnheiter et al., Physicochemical and Antigenic Properties of Synthetic Fragments of Human Leukocyte Interferon. Nature 294: 278-280, 1981.

Arnon, R., Synthetic Peptides as the Basis for Vaccine Design. Molecular Immunology 28(3): 209-215, 1991.

Barbas III et al., Assembly of Combinatorial Antibody Libraries on Phage Surfaces: The Gene III Site. Proc. Natl. Acad. Sci. USA 88: 7978-7982, 1991.

Bittner et al., Molecular Classification of Cutaneous mMlignant Melanoma by Gene Expression Profiling. Nature 406: 536-40, 2000.

Borrebaeck, Antibodies in Diagnostics-From Immunoassays to Protein Chips. Immunology Today 21(8): 379-381, 2000.

Cazares et al., Discovery of prostate Cancer Biomarkers from Lazer Capture Microdissected (LCM) Cells Using Innovative Proteinchip SELDI Mass Spectroscopy. Proc. of the Annual Meeting of the American Association for Cancer Research, New York, NY, p. 851 (2000).

Chames et al., Antibody Engineering and its Applications in Tumor Targeting and Intracellular Immunization. FEMS Microbiology Letters 189: 1-8, 2000.

Clark et al., Genomic Analysis of Metastasis Reveals An Essential Role for RhoC. Nature 406: 532-35, 2000.

Evans et al., Effect of Anticoagulants and Storage Temperatures on Stability of Plasma and Serum Hormones. Clinical Biochemistry 34: 107-12, 2001.

Haab et al. Protein microarrays for highly parallel detection and quantitation of specific proteins and antibodies in complex solutions. *Genome Biol.* 2, RESEARCH0004.1-RESEARCH0004.13, 2001.

Haupt et al., Plastic Antibodies: Developments and Applications. Trends Biotech. 16: 468-476, 1998.

Hemminki et al., Fine Tuning of an Anti-Testosterone Antibody Binding Site by Stepwise Optimisation of the CDRs. Immunotechnology 4: 59-69, 1998.

Hoogenboom et al, Antibody Phage Display Technology and its Applications. Molecular Immunology 4: 1-20, 1998.

Hoogenboom et al., Natural and Designer Binding Sites Made by Phage Display Technology. Immunology Today 21(8): 371-378, 2000.

Huang et al., The Plasticity of Dendritic Cell Responses to Pathogens and Their Components. Science 294: 870-75, 2001.

Hughes et al., Functional Discovery via a Compendium of Expression Profiles. Cell 102: 109-26, 2000.

Keyomarsi et al., Cyclin E and Survival in Patients with Breast Cancer. N. Eng. J. Med. 347(20):1566-75, 2002.

Li, Applications of Display Technology in Protein Analysis. Nature Biotechnology 18: 1251-1256, 2000.

Li et al., Application of Microfluidic Devices to proteomics Research: Identification of Trace-Level Protein Digests and Affinity Capture of Target Peptides. Molecular & Cellular Proteomics 1(2): 157-168, 2002.

Lerner, Antibodies of Predetermined Specificity in Biology and Medicine. Advances in Immunology 36: 1-45, 1984.

MacBeath et al., Printing Proteins as Microarrays for High-Throughput Function Determination. Science 289: 1760-63, 2000.

Mariani et al., Immunogenicity of a Free Synthetic Peptide: Carrier Conjugation Enhances Antibody Affinity for the Native Protein. Molecular Immunology 24(3): 297-303, 1987.

Marks et al, By-Passing Immunization: Building High Affinity Human Antibodies by Chain Shuffling. Bio/technology 10: 779-783, 1992.

Nelson et al., Demystified . . . Monoclonal Antibodies. J. Clin. Pathol.: Mol Pathol. 53: 111-117, 2000.

Ohlin et al, Light Chain Shuffling of a High Affinity Antibody Results in a Drift in Epitope Recognition. Molecular Immunology 33(1): 47-56, 1996.

Park et al., Termal Denaturation: A Useful technique in Peptide Mass Mapping. Anal. Chem. 72: 2667-2670, 2000.

Punglia et al., Effect of Verification Bias onScreening for Prostate Cancer by Measurement of Prostate-Specific Antigen. New Eng. J. Med. 349: 335-342, 2003.

Scrivener et al., Peptidomics: A new Approach to Affinity Protein Microarrays. Proteomics 3: 112-128, 2003.

Soderlind et al., Complementary-Determining Region (CDR) Implantation: A Theme of Recombination. Immunotechnology 4: 279-285, 1999.

Soderlind et al., Recombining Germline-Derived CDR Sequences for Creating Diverse Single-Framework Antibody Libraries. Nature Biotechnology 18: 852-856, 2000.

Soloveiv et al., Combinatorial Peptidomics: A Generic Approach for Protein Expression Profiling. Journal of Nanobiotechnology 1: 4-19, 2003.

Vlatakis et al., Drug Assay Using Antibody Mimics Made by Molecular Imprinting. Nature 361: 645-647, 1993.

Werkmeister et al., Multiple Antigenic Determinants on Type III Collagen. Biochem. J. 274: 895-898, 1991.

Zhu et al., Global Analysis of Protein Activities Using Proteome Chips. Science 293: 2101-05, 2001.

Liu et al., Motif-based construction of a functional map for mammalian olfactory receptors, Genomics 81(5): 443-456, 2003.

Cottrell, Peptide Research 7(3): 115-124, 1994.

De Wildt et al., Nature Biotechnology 18(9): 989-994, 2000.

Barry et al. (2003) "Competitive Assay Formats for High-Throughput Affinity Arrays," J. Biomol. Screen. *(3): 257-263.

Erali et al. (1996) "ELISA for Thyoglobin in Serum: Recovery Studies to Evaluate Autoantibody Interference and Reliability of Thyroglobin Values," Clinical Chemistry 42: 766-770.

Hellmold et al. (2002) "Identification of End Points Relevant to Detection of Potentially Adverse Drug Reactions," Toxicology Letters 127: 239-243.

De Wildt et al. (2000) "Antibody Arrays for High-Throughput Screening of Antibody-Antigen Interactions," Nature 18: 969-94.

International Search Report for PCT/EP01/012295, mailed on Apr. 5, 2002.

Kuruvilla et al. (2002) "Dissecting Glucose Signaling with Diversity-Oriented Synthesis and Small-Molecule Microarrays," Nature 416: 653-657.

Lesko et al. (2001) "Use of Biomarkers and Surrogate Endpoints in Drug Development and Regulatory Decision Making: Criteria, Validation, Strategies," Annu. Rev. Pharmacol. Toxicol. 41: 347-366.

Lizardi et al. (1998) "Mutation Detection and Single Molecule Counting Using Isothermal Rolling Circle Amplification," Mat. Genet. 19: 225-232.

Michaud et al. (2003) "Analyzing Antibody Specificity with Whole Proteome Microarrays," Nat. Biotech. 21(12) 1509-12 (e-publication Nov. 9, 2003).

Rosenkranz (2003) "Biomarkers and Surrogate Endpoints in Clinical Drug Development," Applied Clinical Trials, pp. 30-34, 40.

Schweitzer et al. (2002) "Multiplexed Protein Profiling on Microarrays by Rolling-Circle Amplification," Nat. Biotechnol. 20: 359-365.

Sumner et al. (2003) "Plant Metabolomics: large-scale phytochemistry in the functional genomics era," Phytochemistry, Pergamon Press, GB, vol. 62, No. 6: 817-836.

Weckwerth (2003) "Metabolomics in Systems Biology," Annu. Rev. Plant Biol. 54: 669-689.

Whaley et al. (1991) "Identification of Nearest-Neighbor Peptides in Protease Digests by Mass Spectrometry for Construction of Sequence-Ordered Tryptic Maps," Biological Mass Spectrometry 20: 210-14.

* cited by examiner

METHOD FOR ANALYZING PROTEINS

CROSS REFERENCES TO RELATED APPLICATIONS

This application is a continuation of the International Patent Application PCT/EP01/12295 filed on Oct. 24, 2001, designating the U.S., and published in German, which claims priority to German Patent Application DE 100 54 055.4, filed on Oct. 31, 2000, both of which are incorporated herein by reference in their entireties.

BACKGROUND OF THE INVENTION

1. Field of the Invention

The present invention relates to a method for analyzing proteins in which an array of first capture molecules which are specific for peptide epitopes is employed, and to a corresponding capture molecule.

2. Description of the Related Art

Numerous methods of this type are known from the prior art, and they are used for the qualitative or quantitative analysis of proteins.

Examples of the areas of use of the known methods are protein analysis and protein detection. A further novel area of application of the known methods is the area of proteomics, a branch of research devoted entirely to proteins. One aspect of proteomics deals with comparing the protein composition in pathologically altered cells contrasted with normal, healthy cells. Investigations of this type are at present usually carried out by two-dimensional gel electrophoresis. Another field investigates the spatial structure of proteins, which is of interest in particular for drugs companies for developing novel medicaments.

In two-dimensional gel electrophoresis, the protein mixture to be analyzed is applied to a solid support, and a first separation takes place according to the content of acidic and basic amino acid units in the proteins via a pH gradient. The proteins are then fractionated in the second direction by an electric field, to result in a pattern of spots in which each spot represents one protein. It is possible by comparing the patterns of spots to analyze differences in protein compositions between healthy and pathologically altered cells. For identification, the protein spots are cut out and the proteins are fragmented by digestion with specific proteases. The masses of the fragments remaining after this treatment are characteristic of each protein.

In the method mentioned in the introduction for analyzing proteins, the detection takes place, for example, with protein-specific antibodies in array format.

To obtain such protein-specific antibodies, the applicant employs isolated, purified proteins, recombinantly produced proteins or chemically synthesized peptides derived from the protein sequence. The antibodies are obtained by immunization of laboratory animals with the proteins or peptides acting as antigens, and with adjuvants. It is also possible on the other hand to obtain the antibodies by in vitro methods as recombinant antibodies.

The peptides which are to be synthesized chemically are derived from known protein sequences, which are present, for example, in protein databases or can be found from nucleic acid databases, using software programs which allow theoretical predictions to be made about the protein structure and a possible antigenicity. Programs of this type are described, for example, by Lars Hennig: "WinPep—ein Programm zur Analyse von Aminosäuresequenzen", BIOSPEKTRUM 4 (5), 1998, pages 49-50; or by Devereux et al.: "A Comprehensive Set of Sequence Analysis Programs for the VAX", NUCLEIC ACIDS RESEARCH, volume 12, 1984, pages 387-395. With these programs it is possible to list all possible fragments, with molecular weight, sequence, sequence position and length, which are generated on cleavage of proteins for example by proteases or chemical agents. To predict the antigenicity, the probability with which the epitope is located on the surface of the protein is found on the basis of structural predictions; see, for example, Hopp and Woods: "A computer program for predicting protein antigenic determinants", Mol. Immunol., volume 20, 1983, pages 483-489; further literature references are to be found in the worldwide web under the address www.expasy.ch.

Although the antibodies generated through application of these techniques are very good at recognizing the peptide employed for immunization, they often do not bind to the corresponding peptide epitope in the native protein. The reason for this may be, for example, that the peptide epitope in the native protein is not accessible to the antibody, for steric reasons, or that it is present, as a result of post-translational modification, in a modified form which cannot be derived from the database. A further reason may be that the peptide epitope is present in the native protein in a conformation which prevents antibody binding.

Thus, a disadvantage of this technique is the initial elaborate generation of a large number of peptide-specific antibodies against protein epitopes, which subsequently bind only poorly or not at all to the protein which is sought.

Proteins can be detected using such protein-specific antibodies, on the one hand, after fractionation by means of SDS-PAGE and transfer to membranes by Western blotting/immunoblotting techniques or by means of the ELISA technique. In the ELISA technique, the protein to be detected is bound, without previous separation of other proteins from a complete protein solution, directly,to a highly specific antibody which is immobilized on a solid support. The protein solution is then washed off the solid support, and the protein which is bound, i.e. remaining on the support, is detected.

This detection takes place either with the aid of labeled second antibodies which are specific for the bound protein, or by competition of the analyte protein with labeled analyte protein which is added to the solution in defined amounts. This indirect detection makes use of the fact that unlabeled analyte protein from the sample and added labeled analyte protein compete in a manner which is defined by the law of mass action for the binding sites which are present. This results in the amount of bound, labeled analyte protein being inversely proportional to the amount of unlabeled analyte protein in the sample.

This method has on the one hand the previously mentioned disadvantage, namely that the preparation of the specific antibodies leads to a large number of antibodies which bind only poorly or not at all to the protein to be analyzed. A further disadvantage on use of the Western blotting technique is that the protein mixture fractionated by SDS-PAGE can in each case be tested only with one antibody or with differently labeled antibodies, respectively, in order to ensure distinguishability of the antibodies bound to the different proteins.

In the ELISA technique it is also always possible for only one antibody to be immobilized per analysis well and then incubated with the protein solution. This technique requires large amounts of sample because each analysis well must be incubated with one aliquot of the protein mixture. A further disadvantage in the known methods is that detection of the bound proteins requires specific second antibodies for each protein to be detected or large amounts of labeled analyte proteins for competition experiments.

As already mentioned in the introduction, the applicant also functionally immobilizes protein-specific antibodies differing in specificity in array format in rows and columns on a support material. The proteins to be analyzed are labeled and then incubated with the antibodies on the array. The proteins in the solution which are antigens for the immobilized antibodies then bind to the antibodies which are specific for them, resulting in spatially resolved specific protein binding.

It is possible on the basis of the known binding specificities of the immobilized antibodies and of the known positions of the respective antibodies in the array to determine the bound amount of the respective proteins in parallel. For this purpose, the bound amount of protein is measured via the labeling on the proteins by means of a spatially resolved detection.

Besides qualitative parallel detection of different proteins present in the sample solution, it is in addition to that possible by use of standard proteins to determine quantitatively the analyte proteins.

In contrast to the method described above, the advantage here is that a plurality of proteins can be detected in parallel in the same sample and in one well. However, the disadvantage is that the proteins to be analyzed must be labeled, for which purpose appropriate labels must be introduced on particular functional groups of individual amino acids of the proteins. The efficiency of such labeling reactions varies widely for different proteins, and it is determined by the particular immediate microenvironment of a functional group, i.e. by steric shielding, pH variation in the direct vicinity of the functional group due to neighboring groups, salts, solvents etc. In relation to the result, this means that the reactivity of chemically identical functional groups in a protein may vary widely, so that quantitative reaction of certain functional groups is very difficult.

In addition, the labeling reaction may lead to modification of amino acids within an epitope recognized by the specific antibody, which leads to loss of binding between protein epitope and antibody. However, this means that the protein is no longer detectable via the described assay method after the labeling.

SUMMARY OF THE INVENTION

Against this background, an object underlying the present invention is to improve the method mentioned at the outset such that quantitative and/or qualitative analysis of proteins becomes possible in a simple, rapid and reliable way.

According to the invention this object is achieved with the method comprising the steps:
  degradation of the proteins to be analyzed or of a protein mixture containing the proteins to be analyzed to peptide fragments corresponding to the peptide epitopes,
  incubation of the array with the peptide fragments, and
  detection of peptide fragments bound to the first capture molecules.

This object on which the invention is based is completely achieved in this way. The invention is based on the surprising realization by the inventors that the capture molecules immobilized in array format are incubated not as in the prior art with the proteins but after, for example, enzymatic cleavage of the proteins with individual peptide fragments which correspond to the peptide epitopes which are employed for generating the specific first capture molecules.

One advantage of this method is that the secondary and tertiary structures of the proteins to be analyzed are irrelevant, and the first capture molecules recognize the corresponding peptide fragments with great certainty because they were generated against corresponding peptide epitopes. These epitopes can be predicted directly from databases, and additional elaborate prediction of secondary and tertiary structures is unnecessary. The novel method is not only very reliable in this way, it is also simple and quick to carry out because the first capture molecules reliably recognize the proteins via the detected peptide fragments.

A further advantage is to be seen in the fact that each capture molecule recognizes its optimal antigen, since the synthetic peptide used to generate capture molecules is identical to the peptide fragment to be detected. The disadvantage present in the prior art is avoided in this way, namely that it was up to now not possible with proteins to predict whether a peptide-specific antibody also recognizes the native protein. In other words, this means that with the first capture molecules there is a distinct reduction in the rejected material compared with the prior art.

Since the arrangement of the different first capture molecules in the array is known, it is possible by means of an automatable, spatially resolved detection to identify qualitatively and determine quantitatively the fragments and thus the proteins. This is because the peptide patterns found correlate directly with the protein pattern defined as analyte protein on designing the array. It is additionally possible for peptide patterns found to be screened against DNA databases using simple, fast algorithms.

It is possible in this way to obtain information quickly and reliably about which proteins are present in a sample solution, what method can be employed for example in diagnostics. In addition, the novel method makes it possible for the first time to carry out simple analysis of mutations at the protein level.

A further advantage of the known method is its speed, since the low molecular weight fragments permit binding assays to be carried out faster than do higher molecular weight proteins. The result is thus a kinetic speeding up of the assays, and similar kietics of analyte binding lead to simpler establishment of optimal conditions for the assays than is the case with the highly variable kinetics resulting with analyte proteins which vary greatly in their molecular weight.

A further advantage of the novel method is that a defined and complete degradation of the proteins to be analyzed to give the peptide fragments is possible, and that, in contrast to proteins, the fragments can be quantitatively labeled on defined functional groups. This leads to detection of the peptide fragments being possible not only qualitatively but also quantitatively without needing to take account of secondary and tertiary structures.

A further object is the method according to the invention, wherein fragments which are unbound are washed away after the incubation.

The advantage of this is that the specificity of the method is increased in a manner known per se.

A further object is the method according to the invention, wherein the peptide fragments are labeled before the incubation.

Since a specific, complete labeling of the peptide fragments on defined functional groups is possible, quantitative determination of each bound peptide epitope can be carried out in this way. It is advantageous in this connection that complete labeling of the peptide fragments is more easily and more reproducibly possible than labeling of proteins as carried out in the prior art.

A further object is the method according to the invention, wherein the detection takes place via labeled second capture molecules which specifically recognize the peptide fragment bound to the first capture molecule.

It is advantageous here on the one hand that the peptide fragments need not be labeled, so that the method can be carried out overall more quickly, since labeled second capture molecules can be provided in large quantity in a single process step, after which it is then possible to carry out many analytical methods of the invention with different samples of proteins, each of which needs to be degraded only to the corresponding peptide fragments.

A further advantage of this measure is that the selectivity is increased, since peptide fragments nonspecifically bound by the first capture molecule are not recognized because the second capture molecules do not bind to these complexes.

A further object is the method according to the invention, wherein the second capture molecules are generated starting from complexes of first capture molecules and peptide epitopes bound thereto.

The advantage of this is that very specific second capture molecules are generated and can, moreover, be prepared with a high success rate.

A further object is the method according to the invention, wherein the first capture molecules are generated starting from peptide epitopes which are prepared well-aimed in relation to peptide fragments resulted from degradation of the proteins to be analyzed.

This measure is associated with a whole series of advantages. On the one hand, the first capture molecules against the linear peptide epitopes can be produced with a high success rate, because the peptide epitopes for preparing and isolating the capture molecules are completely identical to the peptide epitopes to be analyzed. This leads to considerably less rejected material being produced in the preparation of the first capture molecules than in the preparation of protein-specific capture molecules. Such peptide epitopes for preparing and isolating the capture molecules can be prepared and completely characterized analytically quickly and at low cost, which represents a further advantage compared with the prior art.

In addition, this measure also increases the specificity of the novel method. This is because epitopes occurring in different proteins can be supplemented by further protein-specific epitopes in such a way that the combination of epitopes detected on the array is unambiguous for particular analyte proteins. Not only is there an increase in the specificity and redundancy of the novel method in this way, targeted optimization for detecting particular proteins is also possible.

In this connection, the peptide epitopes can be prepared by chemical synthesis or enzymatic degradation from known proteins, so that inexpensive and fast complete analytical characterization thereof is possible with standard methods.

A further object is the method according to the invention, wherein the well-aimed prepared peptide epitopes are selected from potential peptide epitopes of the proteins to be analyzed.

One advantage in this case is that only peptide epitopes are prepared against which capture molecules can also be generated. This measure thus leads to a saving of time and synthesis for the preparation of the first and/or second capture molecules. "Potential" peptide epitopes mean in this connection all possible epitopes of a protein, i.e. including those which are not present on the surface of the protein and have not to date been used for generating capture molecules. A further advantage in this connection is that many more possible epitopes can be considered for each protein than in the prior art, so that, for example in the case of very similar or closely related proteins, a much larger number of peptide epitopes is available for possible differentiation between the proteins.

A further advantage is that only peptide epitopes are prepared which are indeed specific for a protein or for a few proteins.

A further object is the method according to the invention, wherein the potential peptide epitopes are derived from known amino acid and/or nucleic acid sequences of the proteins to be analyzed.

One advantage in this case is that the peptide epitopes of proteins to be detected are predicted from DNA or protein databases without taking account of the tertiary structure of the proteins. A simple prediction of the protein cleavage sites for the agents employed for a specific protein cleavage is sufficient, a selection being made from one or more peptide epitopes with maximal specificity for the analyte protein. In the optimal case, the epitope occurs only in the analyte protein.

A further object is the method according to the invention, wherein potential peptide epitopes are selected from sequence sections which are retained on degradation of the proteins to be analyzed.

With this measure, the saving of time is advantageous because only capture molecules are generated for which peptide fragments can also be produced, care being taken with the potential peptide epitopes that they are specific for one or for a few analyte proteins and that their preparation is possible with high probability.

Prediction of peptide sequences which are difficult to obtain in chemical synthesis can be employed as further criterion for selecting the peptide epitopes. Conventional prediction of immunogenic linear peptide sequences, in which potential linear peptide epitopes are identified in protein structures on the basis of the hydropathic profiles (Kyte and Doolittle, "A Simple Method for Displaying the Hydropathic Character of a Protein", J. MOL. BIOL. 157 (1982), pages 105-132) and prediction of β-loop-inducing sequence sections (Chou and Fasman, "Prediction of Protein Conformation", BIOCHEMISTRY 13, 1974, pages 222-245), is unnecessary in this case because, after denaturation and degradation of the analyte proteins, all peptide fragments represent potential peptide epitopes, irrespective of their position in the protein structure.

This leads to a larger choice of potential peptide epitopes and thus to a greater probability of finding epitopes specific for proteins to be analyzed (hereinafter: analyte proteins) than with arrays of capture molecules which are incubated with complete analyte proteins.

A further object is the method according to the invention, wherein the well-aimed prepared peptide epitopes are labeled and/or modified like the peptide fragments after/during the degradation of the proteins to be analyzed.

One advantage of this measure is that it leads to a high specificity of the first capture molecules for the peptide fragments, because account is taken even during the preparation of the peptide epitopes used to generate the first capture molecules of whether the peptide fragments are labeled or modified after/during the degradation of the proteins to be analyzed.

A further advantage is to be seen in the well-aimed incorporation of labels in automated chemical synthesis, thus making rapid and low-cost, completely defined labeling possible, which is simpler, less costly and more reproducible than labeling of complete protein.

A further object is the method according to the invention, wherein the well-aimed prepared peptide epitopes are provided with post-translational modifications.

An advantage of this procedure is that the proteins to be analyzed can be screened specifically for post-translational modifications. It is moreover possible to prepare, for example, peptide epitopes from the region of potential phosphorylation sites of a protein as synthetic phosphopeptides and as nonphosphorylated peptides, in order to generate capture molecules for the respective peptide epitopes. An array of such capture molecules which recognize the different phosphorylated and nonphosphorylated peptide epitopes can then be employed to quantify states of phosphorylation of one or more proteins directly from a protein mixture. Other modifications which can be screened in this way include modified amino acids, glycopeptides, etc.

A further object is the method according to the invention, wherein the well-aimed prepared peptide epitopes have at least one amino acid exchange and/or at least one deletion of an amino acid compared with the potential peptide epitopes.

An advantage of this measure is that a single nucleotide polymorphism can be identified, since the exchange or the deletion, respectively, of individual amino acids in proteins can be detected and quantified in this way. For this purpose, epitopes from the region of the amino acid exchange are prepared as synthetic peptides in order to generate specific capture molecules for these epitopes. After enzymatic degradation of the corresponding proteins and, if appropriate, labeling of the generated peptide fragments, and incubation with the array, the various peptides possible through the single nucleotide polymorphism and having the different amino acid exchanges and deletions can be detected and quantified directly on the array.

A further object is the method according to the invention, wherein the or each capture molecule to be an antibody, an antibody fragment, a peptide aptamer or another capture molecule which can be prepared recombinantly by mutation of binding domains or chemical synthesis.

A further object is the method according to the invention, wherein the binding specificity of the capture molecules to be established by binding assays using peptides which have been altered in individual amino acids or in their length. This makes it possible for the specificity of the generated capture molecules to be characterized completely, and rapidly and inexpensively, to avoid cross-reactivity with other epitopes. With proteins themselves this cannot be carried out with reasonable effort.

In one embodiment, the binding specificity of each of the second capture molecules is established by binding assays using peptides which have been varied in individual amino acids or their length.

This can now take place according to the invention in the array with synthetic peptides each of a defined sequence or with peptide libraries against individual immobilized capture molecules and subsequent identification of bound peptides.

Against this background, another object of the present invention is a capture molecule, in particular for use in a method of the above type, which binds specifically to peptide epitopes which correspond to peptide fragments into which the proteins to be analyzed can be degraded, where the peptide epitopes in the protein itself are preferably not accessible to the capture molecule.

With these capture molecules which have not been discoverable in the prior art to date, it is advantageous that they are able very specifically also to distinguish very similar or closely related proteins, because the number of peptide epitopes which are not present on the surface, and which are thus for example masked in the protein itself, is very large. In this way, the number of available peptide epitopes which have not been taken into account in the prior art to date for generating specific antibodies which can be employed for diagnostics, mutation analysis etc. at the protein level is very large.

A further object of the present invention is a capture molecule which specifically binds to a complex of an aforementioned capture molecule and the corresponding peptide epitope.

Such second capture molecules can be used to increase the specificity of the detection assay, as has already been described in detail in connection with the individual steps of the method.

It will be appreciated that the features and advantages which have been mentioned above and which will be explained hereinafter can be used not only in the stated combination but also alone or in another combination without leaving the scope of the present invention.

DETAILED DESCRIPTION OF THE PREFERRED EMBODIMENT

The basic principle of the method for the quantitative and/or qualitative analysis of proteins consists of employing an array of first capture molecules which are specific for peptide epitopes, where there is detection with the protein-specific capture molecules immobilized in the array format, not of proteins but of individual peptide fragments corresponding to the peptide epitopes after, for example, enzymatic cleavage of the proteins.

For this purpose, first potential peptide epitopes or protein sequences are predicted theoretically in protein or gene sequence databases. Since individual epitopes may be split during the enzymatic or chemical cleavage of the proteins to be detected, account must be taken of the cleavage specificity of the proteases used for the protein degradation in order to predict potential peptide epitopes. Potential peptide epitopes which have been predicted theoretically for the individual proteins according to these criteria are prepared by chemical peptide synthesis and labeled on specific functional groups, for example the amino function of the N-terminus or the $\epsilon$-amino group of lysine, for example with fluorophore, biotin etc.

These peptide epitopes then are used for the production, known per se, of antibodies by immunization. The capture molecules produced in this way, which may in the simplest case be antibodies, are then immobilized in rows and columns on the array.

Protein fragments corresponding to the peptide epitopes are obtained by enzymatic or chemical degradation reaction of all the proteins in the entire protein mixture to be analyzed, using specific proteases such as, for example, trypsin, endoprotease Lys C etc., and are then incubated with the array and are detected on the basis of their binding to the first capture molecules.

For detection, it is possible on the one hand to label the resulting peptide fragments with a marker such as, for example, fluorophore, biotin etc., at the same specific functional groups as the synthetic peptide epitopes employed to generate the specific capture molecules. The correspondingly labeled peptides are incubated on the antibody arrays, the unbound peptide fragments are washed away, and the bound peptide fragments are detected site-specifically via their labeling. Since complete labeling of the peptides is possible, each bound peptide epitope can be determined quantitatively.

On the other hand, it is also possible to detect unlabeled peptide epitopes if a labeled second capture molecule is employed, which may in the simplest case be a second antibody which recognizes the peptide bound to the immobilized antibody. This second antibody is generated against the peptide bound on the immobilized antibody, resulting in a drastic increase in the selectivity, because only the specific peptide fragment on the immobilized first antibody is recognized, and peptide fragments nonspecifically bound there are not bound by the second antibody.

In this way, only peptides which represent potential immunogens and which are not fragmented in the protein degradation are employed for the immunization, which leads to a saving of chemical peptide synthesis and the preparation of specific capture molecules, because high-affinity, peptide fragment-specific capture molecules can be produced with a high success rate. This leads to fewer capture molecule rejects than in the preparation of protein-specific capture molecules.

The binding specificity of the capture molecules obtained, in this case therefore antibodies in the array format, can be determined by a binding assay with defined synthetic peptides which have been altered in the individual amino acids. An alternative possibility is also to incubate synthetic peptide libraries which comprise all theoretically possible peptide sequences with individual antibodies immobilized for example on affinity chromatography columns. The peptides bound from the peptide mixtures can be eluted after denaturation of the antibody and be identified by mass spectrometry or by Edman degradation.

It is possible with the novel method for proteins from the degradation of cells, from body fluids or tissues not only to be quantified but, for example, also to be analyzed for post-translational modifications and single nucleotide polymorphisms.

What is claimed is:

1. A method for detecting plural different proteins in a protein mixture, comprising:
   (1) denaturing and fragmenting said proteins to produce linear peptide fragments comprising peptide epitopes;
   (2) providing an array comprising, at known positions on the array, first capture molecules produced using synthetic peptides and being specific for said individual peptide epitopes, whereby the positions of the first capture molecules produce a spatially resolved pattern for identifying the linear peptide fragments and thus proteins that correspond to the linear peptide fragments;
   (3) incubating the array with the linear peptide fragments under conditions whereby the first capture molecules specifically bind to and thereby form complexes with the linear peptide fragments; and
   (4) detecting the linear peptide fragments, if any, bound to the first capture molecules by contacting said complexes with labeled second capture molecules selected from the group consisting of antibodies, antibody fragments, and peptide aptamers.

2. The method of claim 1, further comprising washing away unbound linear peptide fragments after the incubation step.

3. The method of claim 1, wherein each of the first capture molecules is selected from the group consisting of: an antibody, an antibody fragment, a peptide aptamer and another capture molecule which can be prepared recombinantly by mutation of binding domains and by chemical synthesis.

4. The method of claim 1, wherein the binding specificity of each of the second capture molecules is established by binding assays using peptides which have been varied in individual amino acids or their length.

5. The method of claim 1, wherein said individual peptide epitopes used to generate said first capture molecules differ from the corresponding linear peptide fragments by at least one amino acid.

6. The method of claim 1, wherein said individual peptide epitopes are selected from all potential peptide epitopes of said proteins.

7. The method of claim 6, wherein the potential peptide epitopes are derived from known amino acid sequences of said proteins.

8. The method of claim 7, wherein sequence sections which are retained after fragmentation of said proteins are selected as potential peptide epitopes.

9. The method of claim 6, wherein the potential peptide epitopes are derived from known nucleic acid sequences encoding said proteins.

10. The method of claim 6, wherein sequence sections which are retained after fragmentation of said proteins are selected as potential peptide epitopes.

11. The method as claimed in claim 6, wherein said individual peptide epitopes differ by at least one amino acid compared to a potential peptide epitope of said proteins.

12. The method as claimed in claim 1, wherein said first capture molecules are generated to be specific for said individual peptide epitopes, which are provided with post-translational modifications.

13. The method as claimed in claim 1, wherein the binding specificity of the first capture molecules is established by binding assays using peptides which have been varied in individual amino acids or their length.

14. The method of claim 1, wherein said second capture molecules are raised against one of said linear peptide fragments specifically bound to the first capture molecules.

15. The method of claim 1, wherein each of the first capture molecules is an antibody or an antibody fragment.

16. The method of claim 1, wherein each of the second capture molecules is an antibody or an antibody fragment.

17. The method of claim 1, wherein each of the first capture molecules is an antibody.

18. The method of claim 1, wherein each of the second capture molecules is an antibody.

* * * * *